United States Patent
Chang et al.

(10) Patent No.: US 9,341,605 B2
(45) Date of Patent: May 17, 2016

(54) CHEMICAL PROFILE OF DETECTING BIOACTIVE COMPONENTS OF QUINONES, STILBENES, FLAVONES AND ALKALOIDS

(75) Inventors: Fang-Rong Chang, Kaohsiung (TW); Tung-Ying Wu, Kaohsiung (TW); Yang-Chang Wu, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 328 days.

(21) Appl. No.: 13/528,131

(22) Filed: Jun. 20, 2012

(65) Prior Publication Data
US 2013/0000389 A1    Jan. 3, 2013

(30) Foreign Application Priority Data
Jun. 29, 2011   (TW) .............................. 100122952 A

(51) Int. Cl.
*G01N 30/02* (2006.01)
*G01N 30/88* (2006.01)

(52) U.S. Cl.
CPC ........ *G01N 30/88* (2013.01); *G01N 2030/8813* (2013.01)

(58) Field of Classification Search
None
See application file for complete search history.

(56) References Cited

PUBLICATIONS

Dembitsky, V. M., Astonishing Diversity of Natural Suriactants: 5. Biologically Active Glycosides of Aromatic Metabolites, 2005, Lipids, vol. 40(9), pp. 869-900.*
Shi, Y. et al. Cytotoxic and DNA Damage-Inducing Activities of Low Molecular Weight Phenols from Rhubarb, 2001, Anticancer Research, vol. 21, pp. 2847-2854.*
Geng et al., 2008, "Fingerprint of Sanhuang Xiexin Decoction by HPLC," Chinese Traditional and Herbal Drugs 39(4): 525-529.
Feng et al., 2006, "Simultaneous Determination of Three Kinds of Components in Sanhuang Tablets by High-Performance Liquid Chromatography," Acta Pharmaceutica Sinica 41(3): 285-288.
Geng et al., 2011, "Determination of Three Compositions in Cultivated Rheum lhasaense by HPLC," HPLC, 666-668.
Jhou, Sian-Jyun, 2008, "The Influence of Different Processes on the Content of Anthraguinone in Rheum," Journal of Lioling University of TCM 10(10):130.
The Chinese Patent Application Office Action.
Chia-Hsin Su, "Quality Control and Active Components Pharmacokinetics of San-huang-xie-xin-tang," Dec. 21, 2004, Master Thesis Submitted to the National Library, Institute of Pharmacy, Kaohsiung Medical University. **English abstract provided.
Kuo-Ching Wen, 2008, "Establishment of Determination Method for Polyphenol Glycosides in Herbal Medicines," Yearbook of Chinese Medicine and Pharmacy, 4 (26): 81-126.
The Taiwanese Patent Application Office Action. ** English translation is provided.

* cited by examiner

*Primary Examiner* — Robert Xu
(74) *Attorney, Agent, or Firm* — Volpe and Koenig, P.C.

(57) ABSTRACT

Disclosed are a method for analyzing chemical profiles of components from a herbal medicine product. Components may include quinone (including rhein, sennoside A and/or aloe-emodin), stilbene containing resveratroloside, flavone including baicalin, and/or alkaloid including berberine and/or palmatine. The method includes steps of: (a) respectively chromatographing a methanol extract of product and standard(s) corresponding to the component(s) using HPLC; (b) comparing HPLC chromatogram of extract and standard(s); and (c) analyzing the chemical profiles of the product from the comparison results.

17 Claims, 4 Drawing Sheets

CHEMICAL PROFILE OF DETECTING BIOACTIVE COMPONENTS OF QUINONES, STILBENES, FLAVONES AND ALKALOIDS

CROSS-REFERENCE TO RELATED APPLICATION AND CLAIM OF PRIORITY

The application claims the benefit of Taiwan Patent Application No. 100122952, filed on Jun. 29, 2011, in the Taiwan Intellectual Property Office, the disclosures of which are incorporated herein in their entirety by reference.

FIELD OF THE INVENTION

The present invention relates to a chemical profile of the bioactive components. In particular, the present invention relates to a chemical profile of detecting the bioactive components of quinones, stibenes, flavones and alkaloids.

BACKGROUND OF THE INVENTION

*Rheum palmatum* is a herbaceous perennial of the genus *Rheum* in the family Polygonaceae, and it is usually used as a laxative and dampness-drying drug in the Chinese medicine. The rhizomes of *R. palmatum* contain quinones, such as emodin and rhein, etc., which thus are used as the pharmaceutical components for weight-losing and slimming. While the leaves of *R. palmatum* contain senna fructus. The active compounds in *R. palmatum* includes sennoside B, sennoside A, aloe-emodin, emodin and chrysophanol, etc.

*Scutellaria baicalensis* is a herbaceous perennial of the genus *Scutellaria* in the family Lamiaceae, and its root has effects, such as heat-clearing and dampness-drying, laxity and detoxification, hemostasia, and anti-abortion, as well as in the treatment of upper respiratory tract infection and gastroenteritis, in the Chinese medicine pharmacology. The active compounds of *S. baicalensis* include baicalin, oroxylin A-glucuronide, wogonin-7-O-glucuronide, baicalein, wogonin and oroxylin A, etc.

*Coptidis rhizome* is a herbaceous perennial of the genus *Coptidis* in the family Ranunculaceae, and it can be used in treating heat-dampness on stomach and intestines, and diarrhea and emesis. The rhizomes of *C. rhizome* contain berberine. The hydrochloride form of berberine has been used in treating bacterial dysentery and gastroenteritis. Palmatine, which is further extracted from *C. rhizome*, is used in treating jaundice, dysentery, hypertension, inflammation, and hepatic diseases, etc. The active compounds of *C. rhizome* include berberine, columbamine, jatrorrhizine, epiberberine, coptisine and palmatine, etc.

The most famous Chinese medicinal complex formula containing *R. palmatum*, *S. baicalensis* and *C. rhizome* is San-Huang-Xie-Xin-Tang (SHXXT), which has the functions of laxity and dampness-drying and is used in mainly treating diseases such as low stamina and hematemesis, etc. In addition, SHXXT also has effects on anti-inflammation, anti-hypertension, anti-cancer, anti-virus and enteroprotection. However, since SHXXT is a Chinese medicinal complex formula and its components are complicated, the quality of SHXXT is difficult to be controlled. Furthermore, the technology, which would be announced to examine or determine the Chinese medicinal complex formula, the Chinese medicinal single formula or the healthcare food containing *R. palmatum*, *S. baicalensis* and *C. rhizome* does not appear in the market. Therefore, the chemical profile of the Chinese medicine products obtained by quickly and efficiently analyzing and determining the Chinese medicine products would be the powerful detection tool.

It is therefore attempted by the applicant to deal with the above situation encountered in the prior art.

SUMMARY OF THE INVENTION

In the present invention, four groups of compounds (also nominated as bioactive components), including quinones, stilbenes, flavones and alkaloids, are selected to be the quality control standard for the products such as Chinese medicinal complex formulas, single formulas, food and healthcare food, etc. In particular, rhein (4,5-dihydroxy-9,10-dioxo-9,10-dihydroanthracene-2-carboxylic acid, formula I), sennoside A ((9R)-9-[(9R)-2-carboxy-4-hydroxy-10-oxo-5-[(2S,3R,4S,5S,6R)-3,4,5-trihydroxy-6(hydroxymethyl)oxan-2-yl]oxy-9H-anthracen-9-yl]-4-hydroxy-10-oxo-5-[(2S,3R,4S,5S,6R)-3,4,5-trihydroxy-6-(hydroxymethyl)oxan-2-yl]oxy-9H-anthracene-2-carboxylic acid, formula II) and aloe-emodin (1,8-dihydroxy-3-(hydroxymethyl)anthracene-9,10-dione, formula III) in the quinone, resveratroloside ((2R,3S,4R,5R,6S,E)-2-(4-(3,5-dihydroxystyryl)phenoxy)-6-(hydroxymethyl)-tetrahydro-2H-pyran-3,4,5-triol, formula IV) in the stilbene, baicalin ((2S,3S,4S,5R,6S)-6-(5,6-dihydroxy-4-oxo-2-phenyl-4H-chromen-7-yloxy)-3,4,5-trihydroxytetrahydro-2H-pyran-2-carboxylic acid, formula V) in the flavone, and berberine (9,10-dimethoxy-5,6-dihydro[1,3]dioxolo[4,5-g]isoquino[3,2-a]isoquinolin-7-ium, formula VI) and palmatine (2,3,9,10-tetramethoxy-5,6-dihydroisoquinolino[2,1-b]isoquinolin-7-ium, formula VII) in the alkaloid are selected to be the detection targets. The chemical structures of formulas I to VII are shown as follows.

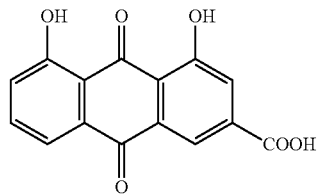

Formula I

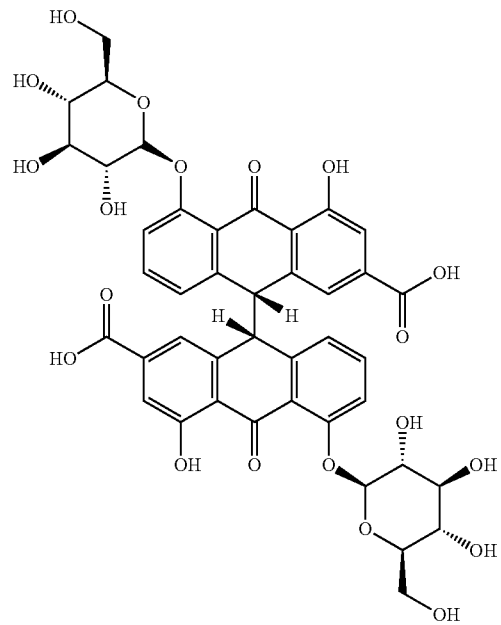

Formula II

-continued

Formula III

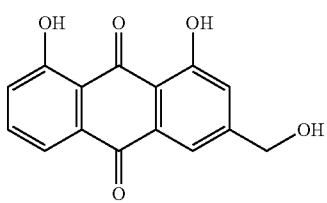

Formula IV

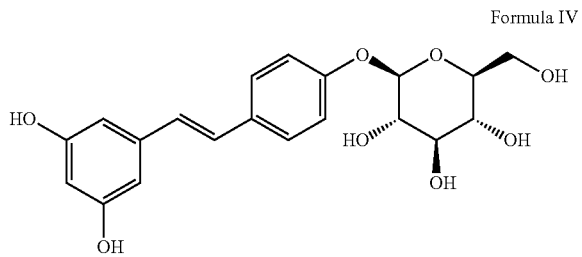

Formula V

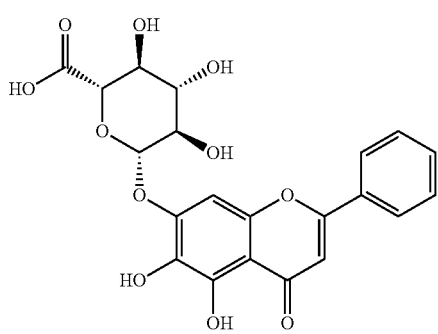

Formula VI

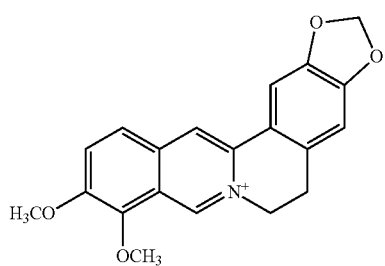

Formula VII

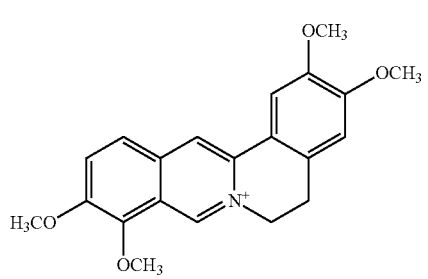

The detection technology of the present invention can be used to detect the complex formula medicines containing R. palmatum, S. Baicalensis and/or C. rhizome, the single formula medicines containing R. palmatum, S. Baicalensis or C. rhizome, or whether at least one of the aforementioned four groups of compounds or at least one of the aforementioned seven specific components are represented in other Chinese medicinal samples. Furthermore, the ratio of these groups of compounds or the specific components in the complex formula medicines, the single formula medicines or the samples are detected.

Therefore, the present invention provides a method for analyzing a chemical profile of a compound in a product. The compound contains at least one ingredient, including rhein, sennoside A, aloe-emodin, resveratroloside, baicalin, berberine and/or palmatine. The method includes steps of: (a) chromatographing a methanol extract of the product and a standard corresponding to the compound; (b) comparing a first high performance liquid chromatography (HPLC) chromatogram of the methanol extract and a second HPLC chromatogram of the standard; (c) determining the product including R. palmatum when at least one first signal responding to rhein, sennoside A, aloe-emodin and/or resveratroloside appears in the first HPLC chromatogram; (d) determining the product including S. baicalensis when a second signal responding to baicalin appears in the first HPLC chromatogram; and (e) determining the product including C. rhizome when a third signal responding to berberine and/or palmatine appears in the first HPLC chromatogram.

The prevent invention further provides a method for analyzing a chemical profile of a compound in a product. The types of the compound includes quinone, stibene, flavone and/or alkaloid. The method includes steps of: (a) respectively chromatographing a methanol extract of the product and a standard corresponding to the compound using HPLC; (b) comparing a first HPLC chromatogram of the methanol extract with a second HPLC chromatogram of the standard; and (c) analyzing the chemical profile of the product according to a result of the step (b).

Preferably, the method further includes a step (a0) of extracting the product with a methanol solution to obtain the methanol extract, wherein the methanol solution has a concentration between 50% and 100%, and the product over the methanol solution has a weight/volume ratio of 1:1.

Preferably, step (b) further comprises a step (b1) of comparing the at least one first peak represented in the first HPLC chromatogram with the at least one second peak represented in the second HPLC chromatogram.

Preferably, the step (b) further comprises a step (b1) of comparing the at least one first retention time represented in the first HPLC chromatogram with the at least one second retention time represented in the second HPLC chromatogram.

The product originates from a botanical plant being selected from R. palmatum, S. baicalensis and/or C. rhizome. Preferably, the product includes 1~3 parts by weight of R. palmatum, 0.5~1.5 parts by weight of S. baicalensis and 0.5~1.5 parts by weight of C. rhizome. Alternatively, R. palmatum, S. baicalensis and C. rhizome have a weight ratio of 2:1:1. In addition, the product includes the dried rhizomes of R. palmatum and C. rhizome and the dried root of S. baicalensis.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1:
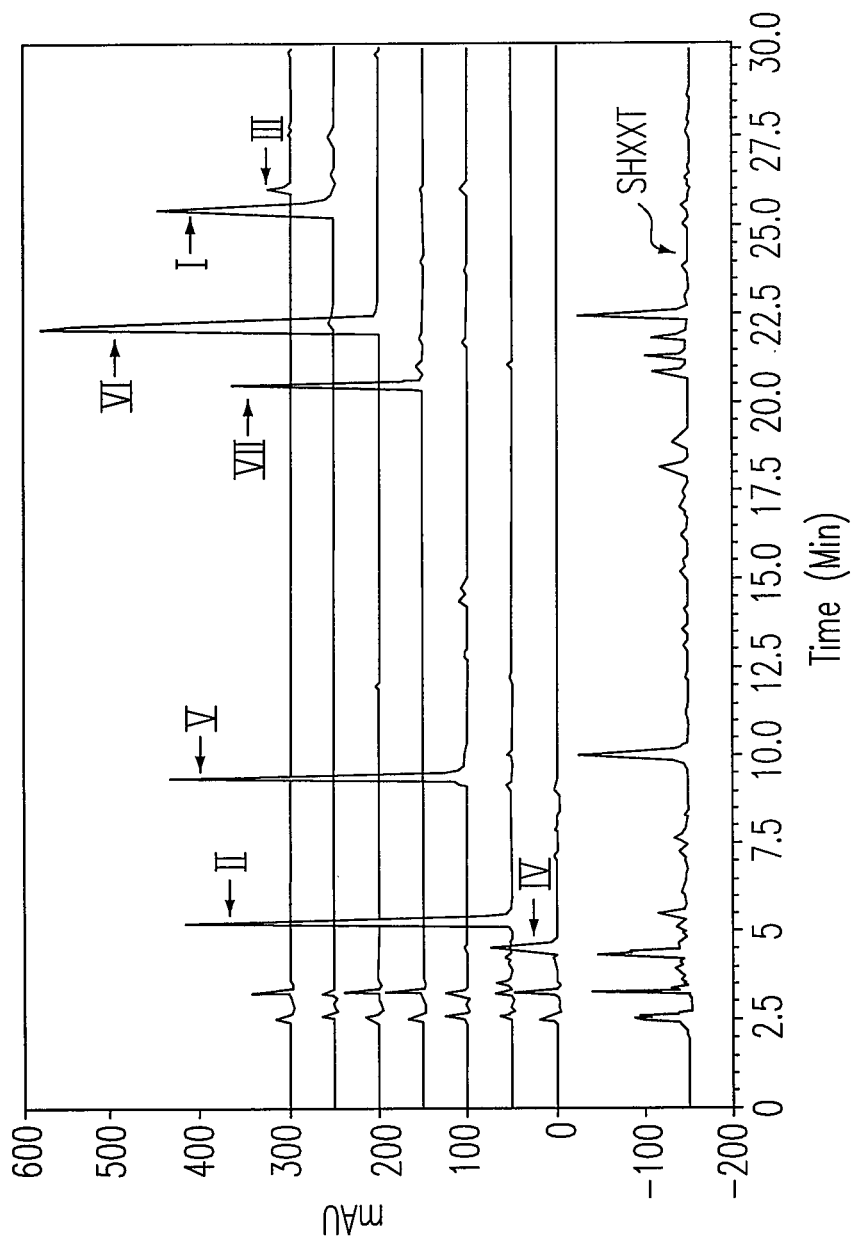
FIG. 1 depicts the HPLC chromatogram of SHXXT in comparison with those of seven compounds (formulas I to VII), wherein SHXXT represents the signals of seven compounds (formulas I to VII).

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

I. Safety of San-Huang-Xie-Xin-Tang (SHXXT) in Animal Model

The most common side effect of SHXXT in clinic is enterorrhea, and SHXXT's safety should be considered for long term usage. This experiment was made on studying whether mice who were administrated different SHXXT formulation gained enterorrhea, so as to evaluate the feasibility of administrating SHXXT for long term usage. Experimental mice were C57BL/6 strain with about 30 g body weight, and the actual body weight of each mice was recorded at the beginning. SHXXT (9 mg/30 g body weight/day) was fed to mice at week 1, and the body weight was recorded every day. SHXXT was not fed to the mice of the control group. Please refer to Table 1, the excrement of mice which was fed formulation 3 (SHXXT 3) at week 1 mainly was solid, and the body weight did not significantly reduced. SHXXT of double dose (18 mg/30 g body weight/day) was fed to mice at week 2, and the body weight was recorded every day. Similarly, the significantly reduced body weight was not found, and the significantly soft stools or liquefied enterorrhea were not found. Therefore, SHXXT with different formulations did not result in the decrease of body weight for long term usage, did not result in the side effect such as dysentery, and could be the Chinese medicinal complex formula with safety.

TABLE 1

| Group | Mouse No. | Weight (g)/week | | | Weight change (g) | |
|---|---|---|---|---|---|---|
| | | Week 0 | Week 1 | Week 2 | Week 0~1 | Week 0~2 |
| Control | 1 | 31.9 | 31.3 | 31.1 | −0.6 | −0.85 |
| | 2 | 31.2 | 30.3 | 30.0 | −0.9 | −1.25 |
| SHXXT 1 | 1 | 30.1 | 29.6 | 30.3 | −0.51 | 0.19 |
| | 2 | 31.8 | 30.2 | 31.4 | −1.56 | −0.36 |
| | 3 | 31.3 | 31.0 | 31.0 | −0.32 | −0.37 |
| SHXXT 2 | 1 | 28.8 | 28.2 | 26.8 | −0.62 | −2.02 |
| | 2 | 30.3 | 30.2 | 29.8 | −0.17 | −0.52 |
| | 3 | 27.4 | 27.7 | 27.8 | 0.23 | 0.33 |
| SHXXT 3 | 1 | 30.3 | 29.7 | 29.4 | −0.6 | −0.9 |
| | 2 | 30.2 | 30.1 | 29.4 | −0.11 | −0.81 |
| | 3 | 30.12 | 30.7 | 30.5 | 0.58 | 0.38 |

II. Preparation of Methanol Extract of SHXXT

In the present experiment, SHXXT powder including *R. palmatum*, *S. baicalensis* and *C. rhizome* is used as the material to be extracted to afford the SHXXT extract, and *R. palmatum*, *S. baicalensis* and *C. rhizome* have a weight ratio of dried materials of 2:1:1. At first, dried SHXXT powder (20 g) was added in 50% methanol solution at a ratio (weight/volume) of 1:1 and sonicated for 30 minutes. The mixture was filtered with filter paper, and the supernatant after filtration was harvested. The supernatant was centrifuged at 3,000 rpm for 15 minutes to withdraw the precipitates. The supernatant behind centrifugation was concentrated, dried and stored at −4° C., and this product is the methanol extract of SHXXT.

If the other Chinese medicinal single formulas containing *R. palmatum*, *S. Baicalensis* or *C. rhizome* or Chinese medicinal complex formulas containing the combination of *R. palmatum*, *S. Baicalensis* and/or *C. rhizome* were the material, the preparation of the methanol extract also was made according to the aforementioned similar procedure. In addition, *R. palmatum* dried rhizome was used, *S. Baicalensis* dried root wad used, and *C. rhizome* dried rhizome was used. The parts by weight of *R. palmatum*, *S. Baicalensis* and *C. rhizome* were ranged at 1~3, 0.5~1.5 and 0.5~1.5, respectively. The preferred concentration of methanol solution was ranged 50% to 100%. The skilled person in the art can formulate the SHXXT methanol extract by adjusting the ratio of the parts by weight of three herbals and the concentration of methanol solution depending on the experiment requirements.

III. High Performance Liquid Chromatography of SHXXT

The HPLC equipment used in this experiment was fabricated by the following apparatuses purchased from Shimadzu, Kyoto Japan, including the systematic controller (LC-10AVP HPLC system), the quaternary bump (LC-10AT), the on-line degasser (DGU-14A), the auto-sampler (SIL-10AD), and the photodiode array detector (SPD-M10A). The chromatography column was Poroshell 120 SB-C18 HPLC column (5 μm, 150 mm×4.6 mm I.D., Agilent Technologies, Inc., U.S.A.). The injection volume of sample was 10 μl.

The mobile phase was prepared by mixing acetonitrile (solvent A) with 4 mM ammonium acetate (solvent B, pH value being adjusted to 3.5 using formic acid). Flow rate of column was 0.6 ml/min, column temperature was ambient temperature, and the detection wavelength was 254 nm. The retention time of the respective independent absorption peaks was compared with that of the standard, and the result was the identification basis for the chemical profile of SHXXT. Gradients of elution sequentially were 22% A to 24% A for 0.01 to 3 minutes, 24% A to 25% A for 3 to 9 minutes, 25% A to 26% A for 9 to 10 minutes, 26% A to 50% A for 10 to 14 minutes, 50% A to 51% A for 14 to 21 minutes, 51% A to 52.5% A for 21 to 25 minutes and 52.5% A to 60% A for 25 to 30 minutes. The skilled person in the art can adjust time of gradient elution and the concentration of the corresponding solvent A depending on the experiment requirements.

At the beginning, seven standards (formulas I to VII) respectively were processed the qualitative analysis to determine the retention time of each compound, and then HPLC was performed on the methanol extract of SHXXT to determine the retention time of each independent absorption peaks of SHXXT. By the comparison with the standards, the HPLC chromatogram of SHXXT methanol extract and seven standards were obtained and shown in FIG. 1 and retention time thereof was listed in Table 2.

TABLE 2

Retention time of seven compounds in the methanol extract of SHXXT

| Compound | Chemical formula | Retention time (Min) |
|---|---|---|
| Resveratroloside | IV | 4.5 |
| Sennoside A | II | 5.2 |
| Baicalin | V | 9.2 |
| Palmatine | VII | 20.4 |
| Berberine | VI | 22.1 |
| Rhein | I | 25.3 |
| Aloe-emodin | III | 25.9 |

IV. HPLC of *R. palmatum, S. baicalensis* and *C. rhizome*

Figure 2:
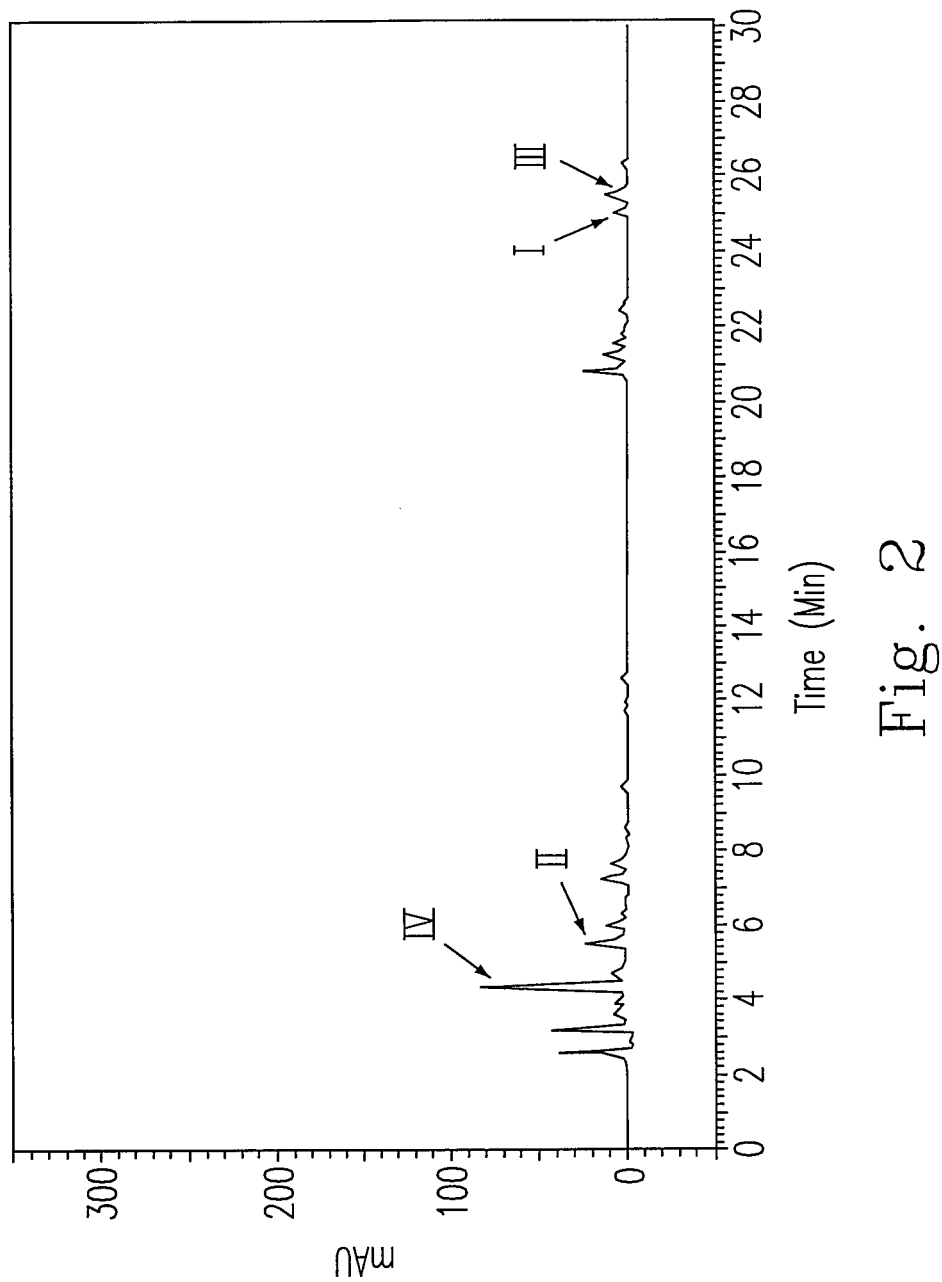
FIG. 2 depicts the HPLC chromatogram of R. palmatum single formula, which represents the absorption peaks of rhein (formula I), sennoside A (formula II), aloe-emodin (formula III) and resveratroloside (formula IV).
Figure 3:
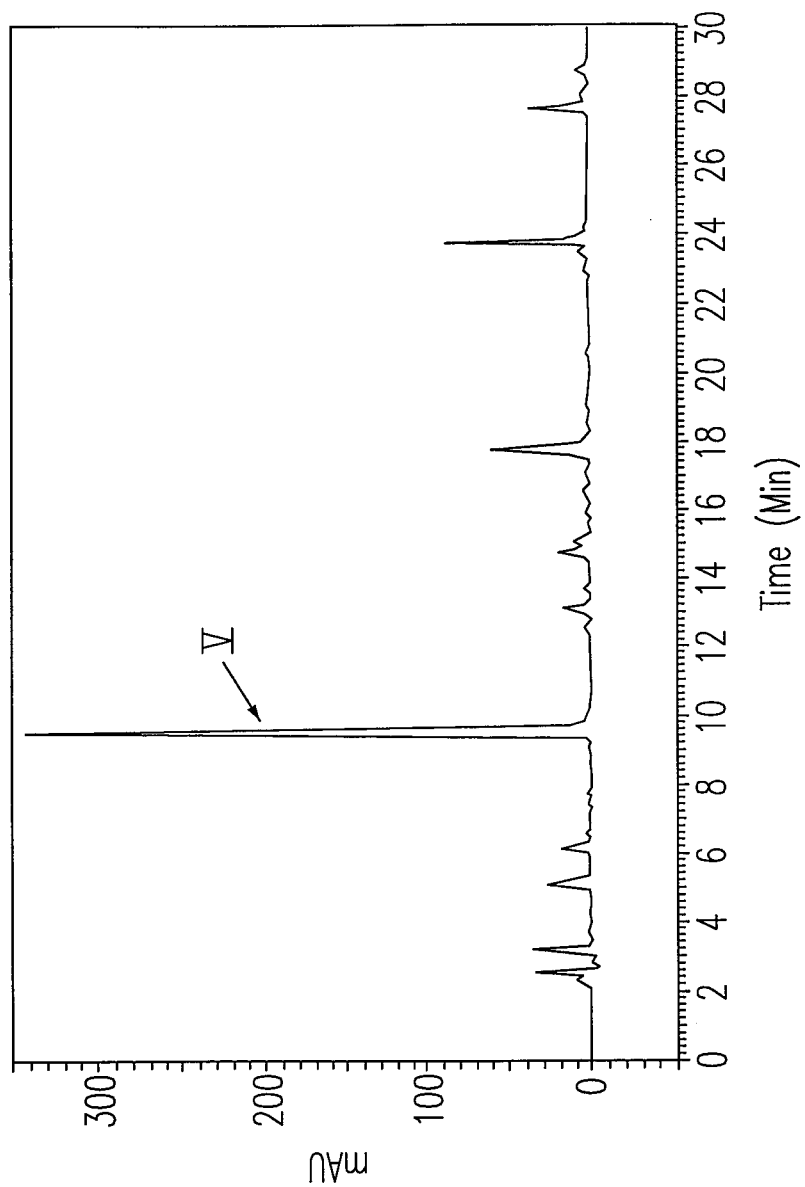
FIG. 3 depicts the HPLC chromatogram of *S. baicalensis* single formula, which represents the absorption peak of baicalin (formula V).
Figure 4:
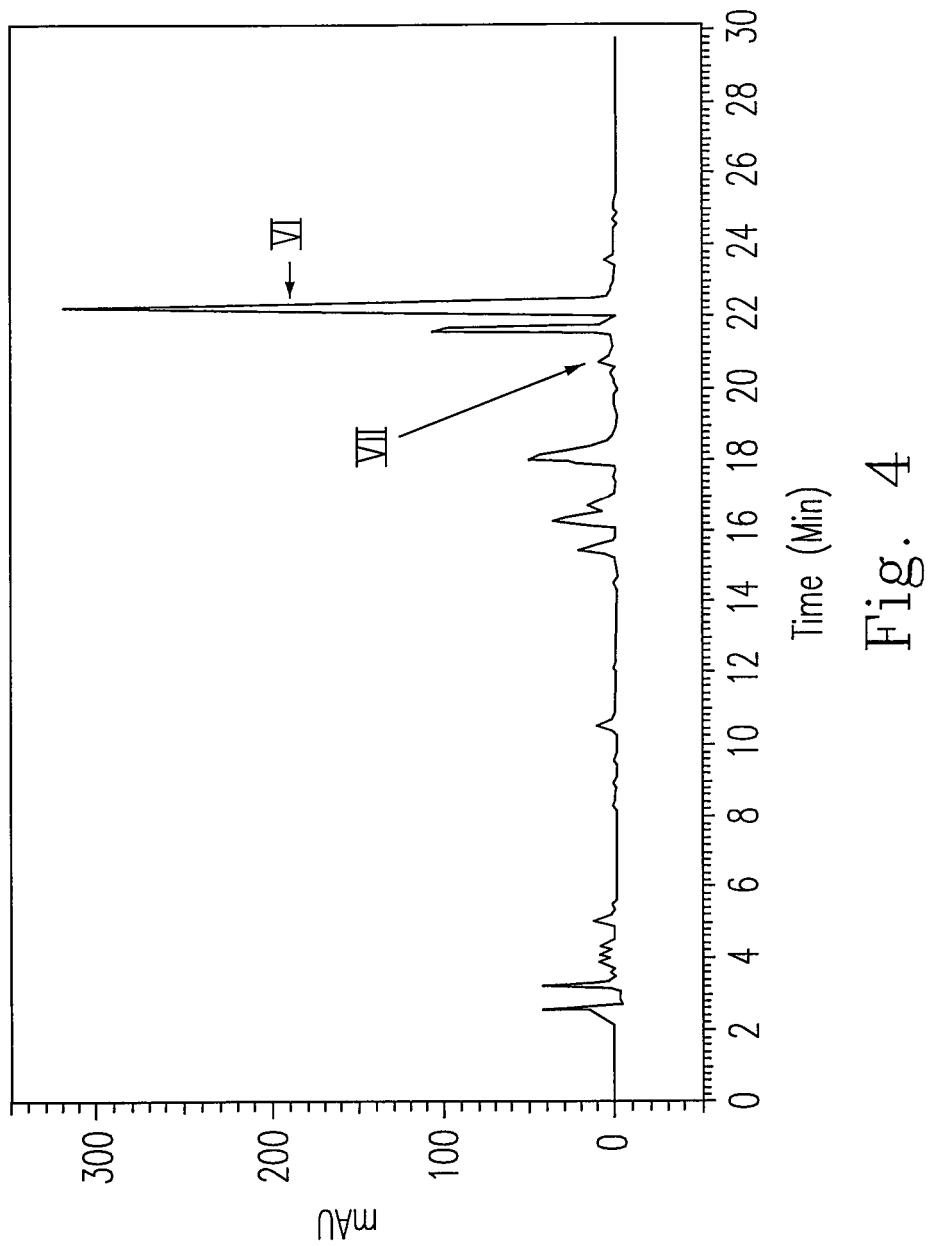
FIG. 4 depicts the HPLC chromatogram of *C. rhizome* single formula, which represents the absorption peaks of berberine (formula VI) and palmatine (formula VII).

According to the aforementioned extraction method and HPLC assay, *R. palmatum* methanol extract, *S. Baicalensis* methanol extract and *C. rhizome* methanol extracts respectively were prepared on the basis of the components of single formula, i.e. *R. palmatum, S. baicalensis* and *C. rhizome*, of SHXXT. The aforementioned three methanol extracts respectively were processed using HPLC to determine the retention time of the absorption peaks of three methanol extracts. The absorption peaks of three methanol extracts were compared with those of the above seven standards, alternatively, the retention time of three methanol extracts were compared with those of the above seven standards, and whether any standard was contained in three methanol extracts was determined. Please refer to FIG. 2, the HPLC chromatogram of *R. palmatum* sequentially showed the absorption peaks of formulas IV, II, I and III, indicating that *R. palmatum* methanol extract contained resveratroloside, sennoside A, rhein and aloe-emodin. Please refer to FIG. 3, similarly, the HPLC chromatogram of *S. baicalensis* showed the absorption peak of formula V, indicating that *S. baicalensis* methanol extract contained baicalin. It was known from FIG. 4 that *C. rhizome* methanol extract contained berberine and palmatine.

In addition, since seven standards respectively had the specific absorption peaks, the standards of rhein, sennoside A and aloe-emodin could be mixed as a quinone compound (or named as a quinone standard), the standard of resveratroloside was defined as a stilbene compound (or named as a stilbene standard), the standard of baicalin was defined as a flavone compound (or named as a flavone standard), and the standards of berberine and palmatine were mixed as an alkaloid compound (or named as an alkaloid standard). The SHXXT complex formula, *R. palmatum* single formula, *S. baicalensis* single formula, *C. rhizome* single formula or their complex formulas were processed using the methanol extraction. The aforementioned extracts and the quinone standard, the stilbene standard, the flavone standard or the alkaloid standard were processed using HPLC chromatography, and their absorption peaks and the retention time were compared to identify the respective components in SHXXT, the single formula or the complex formula, so that their chemical profile analyses were done.

Therefore, in the present invention, the HPLC technology in combination with the photodiode array detector was used to detect whether the products such as Chinese medicinal signal formula or complex formula contain the bioactive components such as quinones, stilbenes, flavones or alkaloids, so that the chemical profiles of the products can be established.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for analyzing a chemical profile of a compound in a product, wherein the compound comprises a sennoside A, a resveratroloside having a structural formula of

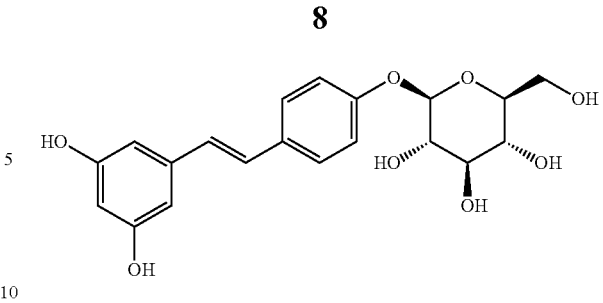

and at least one component selected from the group consisting of a rhein, an aloe-emodin, a baicalin, a berberine, a palmatine and a combination thereof, and the product originates from a botanical plant being selected from the group consisting of a *Rheum palmatum*, a *Scutellaria baicalensis*, a *Coptidis rhizome* and a combination thereof, the method comprising steps of:
 (a) chromatographing a methanol extract of the product and a standard corresponding to the compound;
 (b) comparing a first high performance liquid chromatography (HPLC) chromatogram of the methanol extract with a second HPLC chromatogram of the standard;
 (c) determining the product comprising the *Rheum palmatum* two first signals respond to the sennoside A and the resveratroloside appearing in the first HPLC chromatogram;
 (d) determining the product comprising the *Scutellaria baicalensis* when a second signal responding to the baicalin appears in the first HPLC chromatogram; and
 (e) determining the product comprising the *Coptidis rhizome* when a third signal responding to at least one of the berberine and palmatine appears in the first HPLC chromatogram.

2. The method according to claim 1, wherein the rhein, the sennoside A and the aloe-emodin belong to a quinone.

3. The method according to claim 1, wherein the resveratroloside belongs to a stilbene.

4. The method according to claim 1, wherein the baicalin belongs to a flavone.

5. The method according to claim 1, wherein the berberine and the palmatine belong to an alkaloid.

6. A method for analyzing a chemical profile of a compound in a product, wherein the compound comprises a resveratroloside having a structural formula of

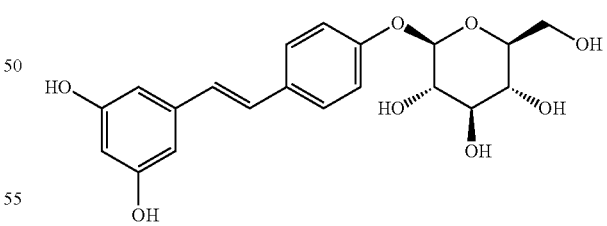

and at least one component being selected from the group consisting of a quinone, a flavone, an alkaloid and a combination thereof, the quinone is selected from the group consisting of a rhein, a sennoside A, an aloe-emodin and a combination thereof, the flavone is a baicalin, and the alkaloid is at least one of a berberine and a palmatine, wherein the product originates from a botanical plant being selected from the group consisting of a *Rheum palmatum*, a *Scutellaria baicalensis*, a *Coptidis rhizome* and a combination thereof, the method comprising steps of:

(a) respectively chromatographing a methanol extract of the product and a standard corresponding to the compound using a high performance liquid chromatography (HPLC);

(b) comparing a first HPLC chromatogram of the methanol extract with a second HPLC chromatogram of the standard; and (c) analyzing the chemical profile of the product according to a result of the step (b).

7. The method according to claim 6, wherein the product comprises 1 to 3 parts by weight of the *Rheum palmatum*, 0.5 to 1.5 parts by weight of the *Scutellaria baicalensis*, and 0.5 to 1.5 parts by weight of the *Coptidis rhizome*.

8. The method according to claim 7, wherein the *R. palmatum*, the *S. baicalensis* and the *C. rhizome* have a weight ratio of 2:1:1.

9. The method according to claim 6, wherein the *R. palmatum* is a dried rhizome.

10. The method according to claim 6, wherein the *S. baicalensis* is a dried root.

11. The method according to claim 6, wherein the *C. rhizome* is a dried rhizome.

12. The method according to claim 6 further comprising a step (a0) of extracting the product with a methanol solution to obtain the methanol extract, wherein the methanol solution has a concentration between 50% and 100%, and the product over the methanol solution has a weight/volume ratio of 1:1.

13. The method according to claim 6, wherein the first HPLC chromatogram represents at least one first peak, the second HPLC chromatogram represents at least one second peak, and the step (b) further comprises a step (b1) of comparing the at least one first peak with the at least one second peak.

14. The method according to claim 6, wherein the first HPLC chromatogram represents at least one first retention time, the second HPLC chromatogram represents at least one second retention time, and the step (b) further comprises a step (b1) of comparing the at least one first retention time with the at least one second retention time.

15. A method for analyzing a chemical profile of a compound in a product, wherein the product originates from a *Rheum palmatum* and at least one botanical plant of a *Scutellaria baicalensis* and a *Coptidis rhizome*, and the compound comprises a sennoside A and a resveratroloside having a structural formula of

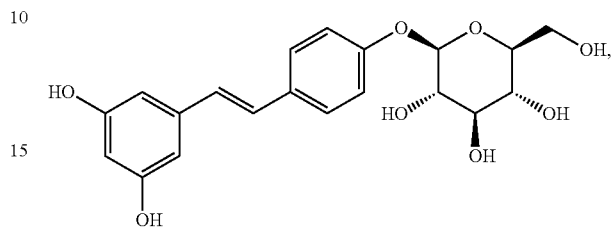

the method comprising steps of:

(a) chromatographing a methanol extract of the product and a standard corresponding to the compound;

(b) comparing a first high performance liquid chromatography (HPLC) chromatogram of the methanol extract with a second HPLC chromatogram of the standard; and (c) determining the product comprising the *Rheum palmatum* when two first signals respond to the sennoside A and the resveratroloside appearing in the first HPLC chromatogram.

16. The method according to claim 15, wherein the compound further comprises at least one of a rhein and an aloe-emodin.

17. The method according to claim 16, wherein the product is determined to comprise the *Rheum palmatum* when two first signals respond to the sennoside A and the resveratroloside, and at least one second signal respond to at least one of the rhein and the aloe-emodin appearing in the first HPLC chromatogram.

* * * * *